United States Patent [19]

Lasker

[11] Patent Number: 5,339,814
[45] Date of Patent: Aug. 23, 1994

[54] PROCESS FOR VISUALIZING TISSUE METABOLISM USING OXYGEN-17

[76] Inventor: Sigmund E. Lasker, 531 Main St., New York, N.Y. 10044

[21] Appl. No.: 869,547

[22] Filed: Apr. 14, 1992

[51] Int. Cl.$^5$ .............................................. A61B 5/055
[52] U.S. Cl. ..................................... 128/653.4; 424/9
[58] Field of Search .......................... 128/653.2, 653.4; 424/9

[56] References Cited

U.S. PATENT DOCUMENTS

| | | |
|---|---|---|
| 4,572,203 | 2/1986 | Feinstein . |
| 4,675,173 | 6/1987 | Widder .............................. 128/653.4 |
| 4,718,433 | 1/1988 | Feinstein . |
| 4,774,958 | 10/1988 | Feinstein . |
| 4,993,415 | 2/1991 | Long ................................. 128/653.4 |
| 4,996,041 | 2/1991 | Arai et al. . |

FOREIGN PATENT DOCUMENTS 9107790 6/1991 World Int. Prop. O. .

OTHER PUBLICATIONS

Guyton, Textbook of Medical Physiology pp. 546–547.

*Primary Examiner*—Ruth S. Smith
*Attorney, Agent, or Firm*—Dressler, Goldsmith, Shore & Milnamow, Ltd.

[57] ABSTRACT

The present invention provides a process for visualizing tissue metabolism in a subject comprising injecting $^{17}O_2$ into the peritoneal cavity of a subject and detecting formed $H_2^{17}O$ in tissues of the subject. The $^{17}O_2$ is injected as a gas or as microbubbles formed from an aqueous protein solution.

7 Claims, No Drawings

PROCESS FOR VISUALIZING TISSUE METABOLISM USING OXYGEN-17

TECHNICAL FIELD OF THE INVENTION

The present invention relates to a process for visualizing tissue metabolism in a subject using a magnetic resonance imaging system and oxygen-17. Oxygen-17 is injected into the peritoneal cavity of a subject as a gas or contained in microbubbles.

BACKGROUND OF THE INVENTION

Magnetic resonance imaging systems rely on the tendency of atomic nuclei possessing magnetic moments to align their spins with an external magnetic field. Because only nuclei with odd numbers of nucleons have a magnetic moment, only those nuclei can be detected and imaged using magnetic resonance. At present, hydrogen with one nucleon, a proton, in its nucleus is the element of choice for diagnostic tissue imaging.

Magnetic resonance imaging data obtained using non-metabolically derived hydrogen, although useful in providing information on tissue perfusion (blood flow to that tissue) and structure, are of limited use in detecting the metabolism of those tissues. Visualization of tissue metabolism using magnetic resonance imaging can be obtained by imaging $H_2O$ formed during aerobic metabolism.

Under aerobic conditions, $H_2O$ is formed as a by-product of oxygen consumption. The metabolic formation of $H_2O$ can be detected using isotopes of oxygen. The most common isotope of oxygen, oxygen-16, has an even number of nucleons and, thus, cannot be imaged in a magnetic imaging system. Another isotope of oxygen, oxygen-15, is unstable with a short half life (radioactive) and its use would expose a subject to potentially harmful radiation.

The oxygen isotope, oxygen-17 ($^{17}O_2$, is stable, has an odd nucleon number and is suitable for use in magnetic resonance imaging. Further, because $^{17}O_2$ can be detected by a proton magnetic resonance imaging in the form of $H_2^{17}O$, the use of $^{17}O_2$ provides data on the metabolic state of imaged tissues.

A magnetic resonance imaging process using $^{17}O_2$ has been previously reported. In accordance with that process, $^{17}O_2$ is administered intravenously in an artificial blood composition comprising perfluorohydrocarbons as the oxygen carrier. See U.S. Pat. No. 4,996,041, the disclosure of which is incorporated herein by reference. Because of the limited oxygen-carrying capacity of perfluorohydrocarbons, that process requires loading the patient with large volumes of the artificial blood composition. Further, the effects of artificial blood compositions per se on tissue metabolism are not yet known.

PCT Patent Publication No. WO 91/07990 reports the use of an inhalant gas containing $^{17}O_2$ as a nuclear magnetic imaging agent. That process requires large volumes of expensive $^{17}O_2$ gas and is limited in its use to subjects having normal respiratory function. Large volumes of inhalant gas are needed in that process because only a small portion of the inhaled gas comes in contact with the blood.

Oxygen absorption into the blood can occur through from the peritoneal cavity. Wilks, S., *J. Appl. Physics*, 14:311 (1939) and Van Liew et al., *Microvascular Research*, 1:257 (1969). Not only does the peritoneal cavity offer a large surface area for absorption (equivalent to that of skin), but also the membrane surfaces in the peritoneal cavity (the peritoneum and the omentum) are readily supplied with capillary vessels that provide ready access to the blood. Indeed, anoxic animals (animals with a deficiency in blood oxygen tension) can be successfully oxygenated with oxygen delivered into the peritoneal cavity. Bilge et al., *Biomaterials, Artificial Cells, Artificial Organs*, 17(4):413 (1989).

BRIEF SUMMARY OF THE INVENTION

The present invention provides a process of visualizing tissue metabolism of a subject comprising injecting $^{17}O_2$ into the peritoneal cavity of a subject and detecting metabolically formed $H_2^{17}O$ using a magnetic resonance imaging system. A benefit of the process of the present invention is the provision of an efficient process of introducing $^{17}O_2$ into tissues for imaging in a magnetic imaging system to detect localized metabolic activity under physiological conditions by monitoring the in vivo metabolism of oxygen via the production and detection of $H_2^{17}O$. A further benefit of the present invention is the provision of an efficient process of introducing $^{17}O_2$ into tissues for imaging in a magnetic imaging system to detect localized metabolic activity in subjects having respiratory dysfunction.

In one aspect, the present invention is directed to a process of visualizing tissue metabolism in a subject comprising the steps of:

a) injecting a gas containing an effective imaging amount of $^{17}O_2$ into the peritoneal cavity of the subject;

b) maintaining the subject for a time period sufficient for the $^{17}O_2$ to be (i) absorbed into the blood stream of the subject, (ii) distributed throughout the tissues of the subject, and (iii) converted to $H_2^{17}O$; and c) detecting the $H_2^{17}O$ with a magnetic resonance imaging system thereby visualizing the tissue metabolism.

The gas containing $^{17}O_2$ is air oxygen carbon dioxide or a mixture of oxygen and carbon dioxide. In a preferred embodiment, the gas is a mixture of about 50 percent by volume oxygen and about 50 percent by volume carbon dioxide. The carbon dioxide can itself contain $^{17}O_2$ and have the formula $C^{17}O_2$.

In another aspect, the present invention contemplates a process of visualizing tissue metabolism in a subject comprising the steps of:

a) injecting microbubbles of substantially uniform diameter that contain an effective imaging amount of $^{17}O_2$ into the peritoneal cavity of the subject;

b) maintaining the subject for a time period sufficient for the microbubbles containing an effective imaging amount of $^{17}O_2$ to be (i) absorbed into the blood of the subject, (ii) distributed throughout the tissues of the subject and (iii) for the $^{17}O_2$ to be converted to $H_2^{17}O$; and c) detecting the $H_2^{17}O$ with a magnetic resonance imaging system thereby visualizing the tissue metabolism.

The microbubbles are formed by subjecting a viscous solution in an atmosphere of $^{17}O_2$ to frequency energy in the range of from about 5,000 Hz to about 30,000 Hz for a time period sufficient to form, but not stabilize the microbubbles. The viscous solution is preferably an aqueous protein solution comprising from about 2 percent by weight to about 10 percent by weight of albumin. In a more preferred embodiment, the viscous solution comprises an aqueous protein solution of about 5 percent by weight of albumin.

DETAILED DESCRIPTION OF THE INVENTION

A Gas Containing $^{17}O_2$

The present invention relates to a process of visualizing tissue metabolism using magnetic resonance imaging of $H_2{}^{17}O$. In accordance with that process, a gas containing an effective imaging amount of $^{17}O_2$ is injected into the peritoneal cavity of a subject; the subject is maintained for a period of time sufficient for the $^{17}O_2$ to be absorbed into the blood stream, distributed to tissues throughout the subject, and converted to $H_2{}^{17}O$. The $H_2{}^{17}O$ formed in a particular tissue is visualized by imaging the tissue with a magnetic resonance imaging system.

As used herein, the term "subject" refers to a mammal and includes human as well as non-human mammals.

The gas containing $^{17}O_2$ can be air (a mixture of about 20 percent by volume oxygen and about 80 percent by volume nitrogen) oxygen ($^{16}O_2$ or $^{18}O_2$), carbon dioxide or a mixture of carbon dioxide and oxygen. Each of those gases can contain from about zero to about 10 percent by volume water as a vapor. Preferably, the water vapor comprises from about 4 percent by volume to about 8 percent by volume of the gas. Gases for use in the present invention are commercially available. By way of example, a mixtures of $^{18}O_2$ and $^{17}O_2$ is commercially available from Isotec Inc., Miamisburg, Ohio.

The gas contains an effective imaging amount of $^{17}O_2$. An effective imaging amount of $^{17}O_2$ is that amount necessary to provide tissue visualization of formed $H_2{}^{17}O$ with magnetic resonance imaging. Means for determining an effective imaging amount in a particular subject will depend, as is well known in the art, on the nature of the gas used, the mass of the subject being imaged, the sensitivity of the magnetic resonance imaging system and the like.

In a preferred embodiment, the gas containing $^{17}O_2$ is a mixture of oxygen and carbon dioxide. The oxygen component of such a mixture can comprise any combination of $^{17}O_2$, $^{18}O_2$ and $^{17}O_2$ so long as an injected volume of the mixture provides an effective imaging amount of $^{17}O_2$. Additionally or alternatively, the carbon dioxide component of such a mixture can contain any combination of $C^{16}O_2$ and $C^{17}O_2$ so long as an injected volume of the mixture provides an effective imaging amount of $^{17}O_2$.

The advantage of using carbon dioxide is that $CO_2$ is absorbed from the peritoneal cavity into the blood stream more readily than oxygen. Further, carbon dioxide enhances the absorption of oxygen across the membranes lining the peritoneal cavity.

The volume of gas injected into the peritoneal cavity of a particular subject is selected inter alia on the basis of subject size and gas composition. The only limitation on injected volume is that the particular volume selected not adversely affect the subject and that the volume contain an effective imaging amount of $^{17}O_2$.

After injection of a gas containing $^{17}O_2$, the subject is maintained for a time period sufficient for (1) the injected $^{17}O_2$ to be absorbed from the peritoneal cavity into the blood (2) the absorbed $^{17}O_2$ to be distributed throughout the subject and enter the tissues of the subject and (3) the $^{17}O_2$ in the tissue to be converted to $H_2{}^{17}O$. Typically, a sufficient time period is from about 20 minutes to about 90 minutes and, preferably from about 20 minutes to about 60 minutes.

Tissue $H_2{}^{17}O$ is visualized by imaging that tissue with a magnetic resonance imaging system. The visualization of tissue $H_2{}^{17}O$ can be accomplished with commercially available magnetic imaging systems such as a General Electric 1.5 T Signa imaging system [1H resonant frequency 63.9 megahertz (MHz)]. Commercially available magnetic resonance imaging systems are typically characterized by the magnetic field strength used, with a field strength of 2.0 Telsa as the current maximum and 0.2 Telsa as the current minimum.

For a given field strength, each detected nucleus has a characteristic frequency. For example, at a field strength of 1.0 Telsa, the resonance frequency for hydrogen is 42.57 MHz; for phosphorus-31 is 17.24 MHz; and for sodium-23 is 11.26 MHz.

B. Microbubbles Containing $^{17}O_2$

In another aspect, the present invention relates to a process of visualizing tissue metabolism using magnetic imaging of $H_2{}^{17}O$ comprising the steps of:

a) injecting microbubbles of substantially uniform diameter that contain an effective imaging amount of $^{17}O_2$ into the peritoneal cavity of a subject, wherein said microbubbles are formed by subjecting a viscous solution in an atmosphere of $^{17}O_2$ to frequency energy in the range of from about 5,000 Hz to about 30,000 Hz for a time period sufficient to form said microbubbles;

b) maintaining said subject for a time period sufficient for said microbubbles containing an effective imaging amount of $^{17}O_2$ to be (i) absorbed into the blood stream of said subject, (ii) distributed throughout the tissues of said subject, and (iii) for said $^{17}O_2$ to be converted to $H_2{}^{17}O$; and c) detecting said $H_2{}^{17}O$ with a magnetic resonance imaging system thereby visualizing said tissue metabolism.

Microbubbles containing $^{17}O_2$ are formed by introducing $^{17}O_2$ into a viscous solution by subjecting the viscous solution to high frequency ultrasonic energy of from about 5,000 Hz to about 30,000 Hz for a time period sufficient to form microbubbles having a diameter of from about 2 microns to about 20 microns and, preferably from about 2 microns to about 4 microns. The time period depends as is well known in the art upon the particular ultrasonic energy used. A procedure for forming microbubbles from viscous solutions can be found in U.S. Pat. Nos. 4,572,203 and 4,774,958, the disclosures of which are incorporated herein by reference.

Exemplary viscous solutions include aqueous media having dissolved or suspended therein from about 40 percent by weight to about 80 percent by weight of a biocompatible polymer such as dextrose or sorbitol. U.S. Pat. Nos. 4,572,203 and 4,774,958.

In a preferred embodiment, a viscous solution is an aqueous protein solution comprising from about 2 percent by weight to about 10 percent by weight of a biocompatible protein such as albumin. Preferably the aqueous protein solution comprises about 5 percent by weight albumin. Microbubbles formed from such a 5 percent by weight albumin solution have a diameter of from about 2 microns to about 4 microns. U.S. Pat. No. 4,774,958.

The viscous solution can further comprise nutrients such as glucose and electrolytes such as sodium, chloride, potassium, calcium and the like.

The high frequency energy level used to form microbubbles is selected so as to form unstable microbubbles of a uniform diameter, which microbubbles break up after injection into the peritoneal cavity releasing $^{17}O_2$ into the peritoneal cavity.

Thus, unlike the method of microbubble formation disclosed in U.S. Pat. Nos. 4,572,203 and 4,774,958, the method of microbubble formation used with the present invention does not involve heat or chemical denaturation and stabilization of formed microbubbles.

In a preferred embodiment, microbubbles for use in the present invention are formed using high frequency energy in the range of from about 5,000 Hz. to about 15,000 Hz.

The following example illustrates a particular embodiment of the present invention and is not limiting of the specification and claims in any way.

EXAMPLE

Example 1

Magnetic Resonance Imaging of Rat Brain

A 400 gram Sprague Dawley rat was anesthetized with sodium pentobarbital (30 mg/kg). About 30 milliliters (ml) of a 50 percent by volume mixture of carbon dioxide and oxygen (50 percent by volume $^{17}O_2$ and 50 percent by volume $C^{16}O_2$) was injected into the peritoneal cavity. Volume changes were analyzed every twenty minutes for a period of 100 minutes after injection. Visualization of $H_2^{17}O$ in brain tissue was monitored over the same period of time.

Direct measurement of volume changes indicated that 28 percent of the oxygen from the gas mixture of carbon dioxide and oxygen was absorbed by 60 minutes after injection.

Magnetic resonance images of the rat brain were performed using a 1.5 Telsa GE Signa system. Imaging was enhanced by the use of a 10 cm solenoid coil placed orthogonal to the field of the Signa. Dilutions of $H_2^{17}O$ in 5mm tubes were placed in the field as references to observe any field changes that might occur during imaging.

Scout images of the brain at repetition times of 3000 milliseconds (ms) and excitation times of 60 ms provided heavily "$T_2$ weighted" images. The slice thickness of the images was 3mm and the images were acquired over a period of 11 minutes. Measurements of contrast at two reference sites in the hypothalamus and cortex were made.

The presence of $H_2^{17}O$ was observed by magnetic resonance imaging 40 minutes after injection. Ninety minutes after injection, no $H_2^{17}O$ could be visualized in the brain.

Although the present invention has been described in terms of certain preferred embodiments, and exemplified with respect thereto, one skilled in the art will readily appreciate that various modifications, changes, omissions and substitutions can be made without departing from the spirit thereof.

We claim:

1. A process of visualizing tissue metabolism in a subject comprising the steps of:
    a) injecting a gas containing an effective imaging amount of $^{17}O_2$ into the peritoneal cavity of said subject;
    b) maintaining said subject for a time period sufficient for said $^{17}O_2$ to be (i) absorbed into the blood stream of said subject, (ii) distributed throughout the tissues of said subject, and (iii) converted to $H_2^{17}O$; and
    c) detecting said $H_2^{17}O$ with a magnetic resonance imaging system thereby visualizing said tissue metabolism.

2. The process according to claim 1 wherein said gas is selected from the group consisting of air, oxygen, carbon dioxide, and a mixture of oxygen and carbon dioxide.

3. The process according to claim 2 wherein said carbon dioxide is $C^{17}O_2$.

4. The process according to claim 1 wherein said gas is a mixture of about 50 percent by volume $^{17}O_2$ and about 50 percent by volume carbon dioxide.

5. A process of visualizing tissue metabolism in a subject comprising the steps of:
    a) injecting microbubbles of substantially uniform diameter that contain an effective imaging amount of $^{17}O_2$ into the peritoneal cavity of a subject, wherein said microbubbles are formed by subjecting a viscous solution in an atmosphere of $^{17}O_2$ to high frequency energy in the range of from about 5,000 Hz to about 15,000 Hz for a time period sufficient to form said microbubbles;
    b) maintaining said subject for a time period sufficient for said microbubbles containing an effective imaging amount of $^{17}O_2$ to be (i) absorbed into the blood stream of said subject, (ii) distributed throughout the tissues of said subject, and (iii) for said $^{17}O_2$ to be converted to $H_2^{17}O$; and
    c) detecting said $H_2^{17}O$ with a magnetic resonance imaging system thereby visualizing said tissue metabolism.

6. The process according to claim 5 wherein said viscous solution is an aqueous protein solution comprising from about 2 percent by weight to about 10 percent by weight of albumin.

7. The process according to claim 6 wherein said aqueous protein solution comprises about 5 percent by weight of albumin.

* * * * *

UNITED STATES PATENT AND TRADEMARK OFFICE
CERTIFICATE OF CORRECTION

PATENT NO. : 5,339,814
DATED : August 23, 1994
INVENTOR(S) : Sigmund E. Lasker

It is certified that error appears in the above-indentified patent and that said Letters Patent is hereby corrected as shown below:

Column 1, line 39, delete [oxygen-17 ($^{17}O_2$,] and insert
--oxygen-17 ($^{17}O_2$),--.

Column 2, line 40, delete [air oxygen] and insert
--air, oxygen,--

Column 3, line 6, delete [A Gas Containting $^{17}O_2$] and insert
--A. Gas Containting $^{17}O_2$--.

Column 3, line 44, delete [$^{7}O_2$,] and insert --$^{16}O_2$,--.

Signed and Sealed this

Twenty-ninth Day of November, 1994

Attest:

BRUCE LEHMAN

Attesting Officer     Commissioner of Patents and Trademarks